Figure 3:
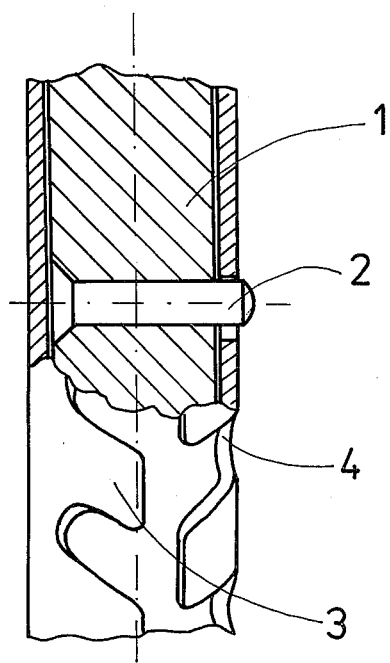

United States Patent [19]

Bacal et al.

[11] 4,404,967

[45] Sep. 20, 1983

[54] SURGICAL STRUT FOR TREATMENT OF THE BACK-BONE

[75] Inventors: Kazimierz Bącal, Akademicka; Lech Wierusz, Browarniany; Stanisław Kossek, Maja, all of Poland

[73] Assignee: Wyzsza Szkola Inzynierska Im. Jurija Gagarina, Zielona

[21] Appl. No.: 456,734

[22] Filed: Jan. 10, 1983

[30] Foreign Application Priority Data

Jan. 18, 1982 [PL] Poland ................................. 234744

[51] Int. Cl.³ ............................................. A61F 5/01
[52] U.S. Cl. ................................... 128/69; 128/92 R; 128/92 E
[58] Field of Search ........................ 128/69, 68, 75, 78, 128/92 R, 92 E

[56] References Cited

U.S. PATENT DOCUMENTS

| | | | |
|---|---|---|---|
| 4,257,409 | 3/1981 | Bacal et al. | 128/69 |
| 4,269,178 | 5/1981 | Keene | 128/69 |
| 4,369,770 | 1/1983 | Bacal et al. | 128/69 |

FOREIGN PATENT DOCUMENTS

| | | | |
|---|---|---|---|
| 2289164 | 5/1976 | France | 128/69 |
| 96695 | 10/1978 | Poland | 128/69 |
| 735248 | 6/1980 | U.S.S.R. | 128/69 |

*Primary Examiner*—Ronald L. Frinks
*Attorney, Agent, or Firm*—Ladas & Parry

[57] ABSTRACT

A surgical strut for the treatment of the back-bone built of a rod having a circular cross-section provided with a thrust pin protruding at one side, a longitudinally cut sleeve mounted on the rod and a pectoral hook and a lumbar hook fitted on spinous processes of vertebrae. Along the cut of the sleeve skew recesses are made which constitute bearing surfaces for the pin mounted in the rod.

One end of the sleeve, closer to the end of the rod, has the outer surface in a form of a cone. On the said surface the pectoral hook rests whose part of the inner surface of the hole is also conical forming the seat for the conical end of the sleeve. The thrust pin, the sleeve and the pectoral hook are situated on the same end of the rod of the strut.

On the other end of the rod the lumbar hook of the known design is mounted. Skew recesses in the sleeve depending on the required adjustment pitch of the length of the strut are situated on the same side or alternately on both sides of the cut of the sleeve.

1 Claim, 3 Drawing Figures

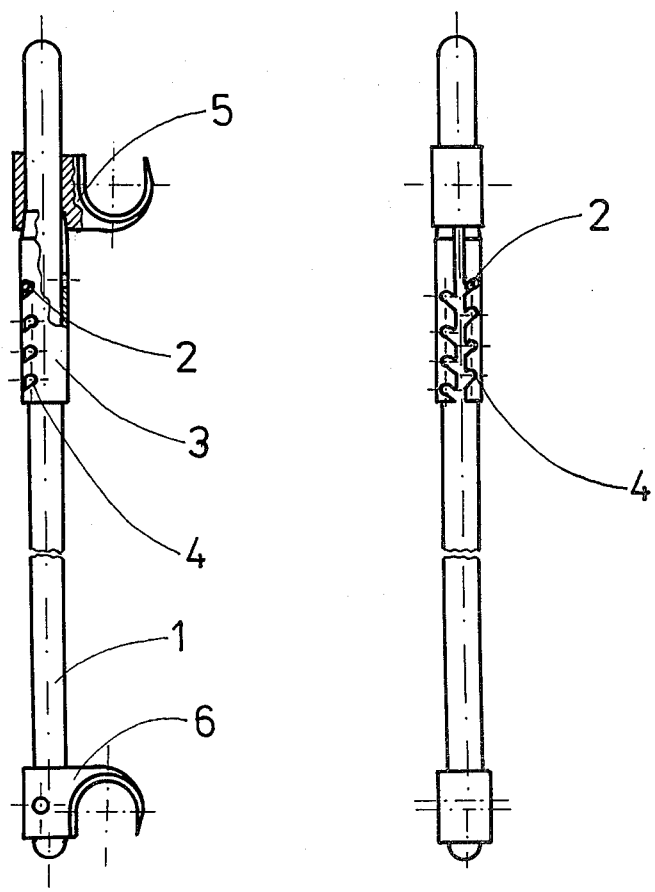

SURGICAL STRUT FOR TREATMENT OF THE BACK-BONE

The subject of the present invention is a surgical strut for the treatment of scoliotic and kyphotic spinal curvatures and the treatment of post-traumatic cases appearing mainly in the lumbar segment of the back-bone.

The treatment of spinal curvatures is realized through an operation consisting in tensioning the back-bone and holding it in the state of prolonged stress over a period of at least a dozen or so months. For this therapy generally known distractors and struts with hook catches are applied. For the post-traumatic treatment of the back-bone in its lumbar segment toothed metal plates serving for stabilization of this segment are used.

Distractors are built of a rod having a circular cross-section provided at one end with conical-cylindrical steps serving for hitching the pectoral hook in a corresponding distance from the lumbar hook attached at the other end of the rod. The disadvantage of distractors is a difficult and labour-consuming technology and low elasticity which causes their breaking in the patient's organism.

Surgical struts according to the Polish Pat. No. 96695 are also made of a circular rod provided at one end with several radial grooves serving for fitting a stopper ring whereupon the pectoral hook rests. The lumbar hook is attached on the other end of the strut. Surgical struts according to the U.S. patent application Ser. No. 06/285,698, now U.S. Pat. No. 4,369,770, are made, like the previous ones, of a rod having a circular cross-section and hooks attached to it. The rod has on one end a number of through holes perpendicular to its axis and serving for fitting a pin, whereas one of the hooks has from the side of the front face in the wall of the circular hole recesses constituting seats for the mounted pin. The disadvantage of both described surgical struts is the existence of a dimensionally small stopper element in a form of a ring or a pin, whose mounting is a hindrance for the course of a surgical operation.

The toothed plate applied for stabilization of injured vertebrae is provided with two double arms with externally sparsely disposed teeth fixed on spinous processes of vertebrae. The toothed plates do not give the possibility of setting the proper position of injured vertebrae and at bending their arms during fixing them on spinous processes they cut them down, thus weakening the stabilization of vertebrae.

The object of the invention is to avoid the inconveniences of the known distractors, struts and toothed plates and the task consists in working out the design of the surgical strut suitable both for the treatment of curvatures and post-traumatic cases of the back-bone, simple in the realization, showing high elasticity and fatigue strength, as well as enabling its easy fitting in the patient's organism, with simultaneous protection against loosening the stopper elements.

This task has been realized in the design of the surgical strut according to the invention, consisting of a rod provided with a thrust pin protruding at one side and a cut stopper sleeve mounted on the rod, wherein along the cut skew recesses are made. Said recesses are the bearing surface for the pin, One end of the sleeve has the outer surface in a form of a cone. On the said surface the pectoral hook rests, whose part of the inner surface of the hole is also shaped conically to form a resistance-clamping seat. The thrust pin is fixed in the rod at the distance from the end of the rod equal to the sum of the length of the sleeve and the height of the pectoral hook. At the same end of the rod the sleeve and the pectoral hook are mounted. At the other end of the rod the lumbar hook of the known design is mounted.

Mounting the conical surface of the pectoral hook on the conical surface of the sleeve causes their automatic stiffening in relation to the rod of the strut, thus securing their free rotation within the limits of the recesses of the sleeve and hindering an uncontrolled change of the position of the hook.

The application of the stopper sleeve in the design of the struts simplifies technologically their production.

The surgical strut according to the invention is characterized by high fatigue strength, enables easy and quick adjustment of the position of the hook, due to which accelerates the course of the operation. Numerous recesses on the stopper sleeve which are situated on one side of its cut or alternately on both sides of the said cut contribute to the fact that the number of particular steps of the length of struts in a dimensional set is four times smaller in relation to the number of steps of the length of the known struts.

The surgical strut according to the invention is shown in an exemplary embodiment in the accompanying drawings wherein FIG. 1 presents the side view of the strut, FIG. 2 presents the rear view of the strut, and FIG. 3 presents the half-section of the fragment of the strut with the rod and the pin and the mounted sleeve.

The strut is made of a rod 1 having a circular cross-section provided with a thrust pin 2 and a sleeve 3 mounted on the rod 1. The sleeve 3 is cut along its axis and at both sides of the cut it has alternately made skew recesses 4. The inner surfaces of skew recesses 4 constitute bearing surfaces for a pin 2. One end of the sleeve 3 situated after mounting it on the rod 1 closer to the end of the rod has the outer surface in a form of a cone. On the said surface a pectoral hook 5 rests whose part of the inner surface of the hole is also in a form of a cone constituting the resistance-clamping seat for the conical end of the sleeve 3. Dimensions of the conical surface of the hole of the pectoral hook 5 correspond to dimensions of the conical surface of the end of the sleeve 3. The sleeve 3 together with the pectoral hook 5 are mounted on the same end of the rod 1 on which the pin 2 is mounted, which is situated in the distance from the end of the rod 1 equal to the sum of the length of the sleeve 3 and the height of the pectoral hook 5. On the other end of the rod 1 terminated with the pin the known lumbar hook 6 is mounted.

What is claimed is:

1. A surgical strut for the treatment of the back-bone consisting of a rod having a circular cross-section and a pectoral- and lumbar hook mounted thereon, characterized in that it has a rod (1) provided with a thrust pin (2) protruding at one side and mounted on one end of the rod longitudinally cut sleeve (3) with skew recesses (4) made along the cut, whereby the end of the sleeve (3) external in relation to the rod (1) has the outer surface in a form of a cone on which a pectoral hook (5) is mounted with the conical inner surface of the hole.

* * * * *